United States Patent [19]

Wu et al.

[11] Patent Number: 5,545,790
[45] Date of Patent: Aug. 13, 1996

[54] PROCESS FOR THE CATALYTIC CYCLODIMERIZATION OF CYCLIC OLEFINS

[75] Inventors: Margaret M. Wu, Skillman, N.J.; Yusheng Xiong, Newtown, Pa.

[73] Assignee: Mobil Oil Corporation, Fairfax, Va.

[21] Appl. No.: 164,272

[22] Filed: Dec. 9, 1993

[51] Int. Cl.$^6$ .................................................. C07C 2/00
[52] U.S. Cl. ........................ 585/510; 585/20; 585/361; 585/520
[58] Field of Search ............................. 585/510, 520, 585/530, 10, 14, 20, 21, 361, 362

[56] References Cited

U.S. PATENT DOCUMENTS

| | | | |
|---|---|---|---|
| 3,258,502 | 5/1964 | Cannel | 260/666 |
| 4,222,800 | 9/1980 | Myers et al. | 149/109.6 |
| 4,410,749 | 10/1983 | Burnette | 585/14 |
| 4,827,064 | 5/1989 | Wu | 585/10 |
| 4,827,073 | 5/1989 | Wu | 585/530 |

OTHER PUBLICATIONS

R. H. Grubbs, et al., JACS, 1978, 100, 7416.
Bird, et al. Tet. Lett., 1961, 373.
Jolly, et al., J. C. S., 1965, 6416.
Arnold, et al., JACS, 1965, 87, 2596.

*Primary Examiner*—P. Achutamurthy
*Attorney, Agent, or Firm*—A. J. McKillop; M. D. Keen

[57] ABSTRACT

A catalytic process for the dimerization of norbornene and/or norbornadiene using a reduced valence state Group VIB metal oxide as the catalyst, preferably Cr(II) on a porous support such as silica. The product norbornene dimer or norbornadiene dimer is obtained in high yield and high stereospecificity at greater than 90 weight percent of the exo-trans-exo stereoisomer. The norbornene dimer is useful as a high energy density fuel. The norbornadiene dimer can be further functionalized to yield novel chemical intermediates or polymerized or copolymerized with other olefins. The norbornadiene dimer can also be hydrogenated for high energy fuel applications.

9 Claims, No Drawings

PROCESS FOR THE CATALYTIC CYCLODIMERIZATION OF CYCLIC OLEFINS

FIELD OF THE INVENTION

This invention relates to a catalytic process for the dimerization of cyclic olefins to produce cyclobutane derivatives. The invention particularly relates to the catalytic dimerization of norbornene and norbornadiene to cycobutane derivatives in high yield and with high stereoisomer selectivity. The invention also relates to the discovery of the use of these cyclobutane derivatives as high energy fuels.

BACKGROUND OF THE INVENTION

Olefin cyclodimerization to cyclobutanes is known in the art and is generally carried out by less efficient photochemical processes. The reaction comprises the [2+2] cyclo-addition of olefins to form the preferred cyclobutane product. However, the photochemical reaction suffers especially from low quantum efficiency. As a possible route to the production of cyclobutanes, the photochemical method for olefin cyclodimerization is also difficult to scale-up into an economically viable process. For example, norbornene, shown structurally herein as (I), is known to dimerize photochemically by [2+2] cyclo-addition to form pentacyclo $[8.2.1.1^{4,7}.0^{2,9}.0^{3,8}]$-tetradecane (II). The dimer is also presented herein as the exo-trans-exo conformational isomer (IIa) and as the exo-trans-endo conformational isomer (IIb). However, the thermal conversion of norbornene to the dimer is unknown in the prior art.

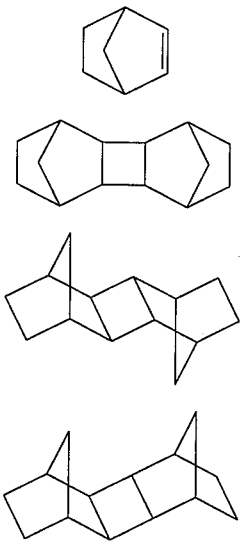

Nonphotolytic olefin dimerizations catalyzed by transition metal catalysts are known but most do not produce cyclobutane derivatives. Activated dienes, however, can be easily cyclodimerized to cyclic dimers, such as the dimerization of norbornadiene (III) to pentacyclo $[8.2.1.1^{4,7}.0^{2,9}.0^{3,8}]$-tetradecadiene-5,11 (IV).

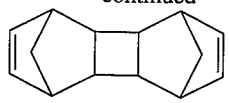

R. H. Grubbs, et al. (*J. Amer. Chem. Soc.* 1978, 100, 7416) prepared cyclobutane from ethylene treated with tris(triphenylphosphene)tetramethylenenickel, but the yields were very low.

Bird, et al. (*Tet. Lett.*, 1961,373) describe the production of norbornadiene dimer, pentacyclo $[8.2.1.1^{4,7}.0^{2,9}.0^{3,8}]$-tetradecadiene-5,11, and related products by dimerization in the presence of certain metal carbonyl compounds, e.g., iron carbonyls, but in low yield.

Jolly, et al. (*J. Chem. Soc.* 1965, 6416), dimerized norbornadiene in contact with dicarbonyldinitrosyliron in near quantitative yield.

Cannel (U.S. Pat. No. 3,258,502) dimerized norbornadiene in contact with tetrakis(trihydrocarbylphosphite) nickel.

Arnold, et al., (*J. Amer. Chem. Soc.*, 1965, 87, 2596) dimerized norbornene through irradiation of the cuprous chloride complex to produce (II) and dimerized norbornadiene in contact with hexacarbonylbis(triphenylphosphine)dicolbalt(O) to provide (IV). Six of the possible twelve stereoisomers of the dimers (II) and (IV) were prepared, separated and characterized.

In U.S. Pat. Nos. 4,827,064 and 4,827,073 to M. Wu, incorporated herein by reference, a unique catalyst system is reported for the preparation of superior hydrocarbon lubricants having low methyl to methylene branch ratio by oligomerization of alpha olefins using reduced valence state Group VIB metal oxide catalyst on porous support. The novel lubricant compositions (referred to as HVIPAO) comprise polyalpha-olefins. The method for their preparation employs as catalyst carbon monoxide reduced chromium on a silica support.

During the course of investigations relating to olefin copolymerization using the foregoing catalyst comprising reduced chromium on a silica support it was discovered that the catalyst is effective for the dimerization of norbornene (I).

Accordingly, it is an object of the present invention to provide a catalytic process for the thermal dimerization of cyclic olefins, particularly norbornene and norbornadiene.

Another object of the present invention is to provide a process for the dimerization of norbornene and/or norbornadiene in high yield and high stereoisomer selectivity.

A further object of the present invention is to provide a novel high energy fuel composition and process for preparing a novel high energy fuel.

SUMMARY OF THE INVENTION

A catalytic process involving a thermal reaction rather than a photochemical reaction for the dimerization of norbornene and/or norbornadiene has been discovered employing reduced valence state Group VIB metal oxide catalyst on porous support. The process provides the norbornene dimer or norbornadiene dimer in high yield and high stereospecificity providing greater than 90 weight percent of the exo-trans-exo stereoisomer. The norbornene dimer is useful as a high energy fuel. The norbornadiene dimer can be further functionalized to yield novel chemical intermediates or polymerized or copolymerized with other olefins. The norbornadiene dimer can also be hydrogenated to provide norbornene dimer for high energy fuel applications.

More particularly, the invention comprises a process for the dimerization of norbornene to produce pentacyclo $[8.2.1.1^{4,7}.0^{2,9}.0^{3,8}]$-tetradecane in high yield with high stereo selectivity. The process comprises contacting norbornene with a reduced valence state Group VIB metal catalyst on a porous support under dimerization conditions whereby said $[8.2.1.1^{4,7}.0^{2,9}.0^{3,8}]$-tetradecane is produced. The preferred catalyst is Cr(II) supported on silica having a pore size of at least 40 Angstroms.

For the dimerization of norbornadiene, the diene is also contacted with a reduced valence state Group VIB metal catalyst on a porous support under dimerization conditions whereby $[8.2.1.1^{4,7}.0^{2,9}.0^{3,8}]$-tetradecadiene-5,11 is produced. Again, the preferred catalyst is Cr(II) supported on silica having a pore size of at least 20 Angstroms.

It has further been discovered that a high energy fuel composition comprises a mixture of $[8.2.1.1^{4,7}.0^{2,9}.0^{3,8}]$-tetradecane and high energy fuel selected from the group consisting of JP-10, RJ-5 and RJ-6. JP-1 0, RJ-5 and RJ-6 are military designations for high energy, high density, synthetic liquid hydrocarbon fuels; RJ-5 is composed of a mixture of isomers of perhydrodinorbornadiene and is commercially available as Shelldyne H™; RJ-6 is a blend of RJ-5 and JP-10, which itself is exo-tetrahydrodicyclopentadiene (exo-THDCP). These fuels are described in U.S. Pat. No. 4,410,749 (Burdette), to which reference is made for a more detailed description of them.

An optional process for the production of a high energy fuel comprises hydrogenating the norbornadiene dimer $[8.2.1.1^{4,7}.0^{2,9}.0^{3,8}]$-tetradecadiene-5,11 and mixing the hydrogenated product with high energy fuel selected from the group consisting of JP-10, RJ-5 and RJ-6.

DETAILED DESCRIPTION OF THE INVENTION

Norbornene (I) cyclo-dimerizes over reduced $CrO_3$ catalyst on silica support, referred to herein as Cr/SiO2, to give a novel [2+2] cyclo-addition product. The catalyst has a high activity of at least 100 turn overs per chromium atom, which is by far the best among the few catalyzed [2+2] reactions. With feed pretreatment and less than one percent catalyst charge, 85% norbornene conversion is obtained and the selectivity to the cyclo-dimer is 90%. The dimer fraction contains three geometric isomers with the exo-trans-exo isomer as the dominant component comprising about 85% of the mixed isomers.

The norbornene dimer (II) is particularly useful as a blending component for high energy density fuel. For example, a 50%:50% blend of the dimer and tetrahydrodicyclopentadiene (JP-10), a current fuel in military application, has a net volumetric heat of combustion of 145,236 BTU/gal, representing a 4% increase over JP10. The extrapolated heat of combustion for the pure norbornene dimer is 151,810 BTU/gal, representing a 7% increase over JP-10.

The bicyclic skeleton of norbornene (I) entails about 19 kcal/mol of strain energy in the molecule. Moreover, the heat of hydrogenation of norbornene is about 5 kcal/mol less than that of unstrained hexene. The latter number is often referred to as olefin strain energy, and is thought to be responsible for the high reactivity of the norbornene double bond in general. The Cr/SiO2 catalyzed cyclodimerization seems to be the result of this unique bicyclic skeleton and attendant strain energy. Other olefins, such as cyclopentene for example, do not undergo this dimerization reaction with $Cr/SiO_2$ catalyst.

The cyclodimerization of norbornene to dimer (II) is formally a [2+2] cyclization. According to molecular orbital theory, the [2+2] thermal reaction is forbidden while the photocyclization of the [2+2] type is allowed. The photolytic cyclodimerization of norbornene, catalyzed or uncatalyzed, has been reported before, as noted herein before. However, the reaction is never practiced on a commercial scale because of the extended UV irradiation time and low energy efficiency of this process. Accordingly, the thermal cyclodimerization of norbornene in the presence of the catalyst which is the subject of the present invention, as opposed to the photochemical reaction, is novel.

The supported catalyst $Cr/SiO_2$ is well known for its activity in olefin polymerization. However, the dimerization of norbornene and norbornadiene using $Cr/SiO_2$ is unprecedented. Other Ziegler type catalysts, such as zirconocene/MAO, catalyze norbornene polymerization in a manner similar to regular olefin addition polymerization. Cationic polymerization of norbornene is also known to occur in the presence of acid catalyst such as $Et_2AlCl+RCl$ to give linear polymers. Nevertheless, the dimerization of norbornene and norbornadiene using $Cr/SiO_2$ is unique, particularly with respect to the yield of dimer and the high degree of stereoselectivity produced.

The dimerization reactions of the invention are catalyzed by supported metal oxide catalysts, such as Cr compounds on silica or other supported IUPAC Periodic Table Group VIB compounds as described in U.S. Pat. No. 4,827,064 to M. Wu. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 20 angstroms are preferred.

The support material usually has high surface area and large pore volumes with average pore size of 40 to about 350 angstroms. The high surface area are beneficial for supporting large amount of highly dispersive, active chromium metal centers and to give maximum efficiency of metal usage, resulting in very high activity catalyst. The support should have large average pore openings of at least 20 angstroms, with an average pore opening of >40 to 300 angstroms preferred. For this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B$, $R_2Mg$, $RLi$, $R_2Zn$, where R is alkyl, alkoxy, aryl and the like. Preferred are CO or $H_2$ or metal alkyl containing compounds.

Alternatively, the Group VIB metal may be applied to the substrate in reduced form, such as CrII compounds. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged at successively higher temperatures to about 600° for a period of about 16 to 20 hours. Thereafter the catalyst is cooled down under an inert atmosphere to a temperature of about 250 to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally the catalyst is cooled down to room temperature and is ready for use.

In the following Examples A–F, the results of which are reported in Table 1, dimerization of norbornene (I) was carried out using $Cr/SiO_2$ catalyst prepared according to U.S. Pat. No. 4,827,064. Norbornene was purchased from Aldrich, and dried as a solution in hexane over molecular sieves and De-Oxy catalyst. In some Examples (B & F), the norbornene in hexane solution was further treated with $Cr/SiO_2$ catalyst at room temperature for 15 min and filtered. Conversion rate was calculated based on weight of crude product. Yield was based on the actual weight of the product isolated.

For Examples A–F, the treated feed was charged either into a glass flask or a Parr reactor containing the catalyst. This slurry was then heated to reaction temperature for about 12 hours. Product isolation consisted of removal of catalyst by filtration, evaporation of solvent and sublimation of the dimers under vacuum.

The crude product from the reactions consists of mainly of about 90 weight percent dimers and the rest are higher oligomers not isolable by sublimation (200° C./0.01 mm Hg). The dimers consist of exo-trans-exo, exo-trans-endo and endo-trans-endo in a ratio of about (85%:13%:2%).

The exo-trans-exo isomer was purified by crystallization from ethanol, and the other two isomers, exo-trans-endo and endo-trans-endo, were identified by comparison of their $^1$H-NMR spectra with those reported in the literature. The 13C-NMR spectrum of the exo-trans-exo isomer consists of only four peaks: 45.1, 38.5, 33.1, 27.3 ppm.

The norbornene conversions depended on pretreatment method for the catalyst or the amount of the catalyst charged to the reactor (Table 1). Treatment with $Cr/SiO_2$ catalyst at room temperature was most effective and convenient to remove any catalyst poisons in the feed and increased norbornene conversion to 84% (Example B). Without any pretreatment and with 9 weight percent catalyst, norbornene conversion was 30% Example A). Other treatment methods, using De-Ox and Molecular sieve, only yielded about 20 weight percent norbornene conversion with 3 weight percent catalyst charged.

The CrSiO2 catalyzed [2+2] cyclodimerization is unsurpassed in its high activity. Catalyst turn over number for Example B is about 100 per Cr atom. Since not all metal sites are active centers, the true catalyst turn over number should be even higher. The previous best turn over number for this [2+2] type reaction is about 25, from ethylene to cyclobutane by nickel catalysts.

TABLE 1

Norbornene dimerization catalyzed by Activated $Cr/SiO_2$

| Example | Catalyst(a), wt % charge | Feed Pretreatment Method | Temp °C. | Time | Conversion |
|---|---|---|---|---|---|
| A | C175, 9% | None | 100 | 5 hr | 30% |
| B | C173, 15% | twice treated with $Cr/SiO_2$ | 95 | 14 hr | 84% |
| C | C173, 3% | De-Ox/Mol Sieve, AlMe3 | 90 | 12 hr | 20% |
| D | C173, 4% | De-Ox/Mol Sieve, | 80 | 6 hr | 22% |
| E | C173, 4% | De-Ox/Mol Sieve, | 80 | 6 hr | 18% |
| F | C175, 7% | twice treated with $Cr/SiO_2$ | 70 | 5 hr | 224 |

(a) Catalyst batch C173 had green color and contained 3 wt % Cr on silica gel. Catalyst batch C175 had blue color and contained 1 wt % Cr on silica gel.

The norbornene dimer product containing three isomers was a solid at room temperature. It was evaluated as a blending component in JP-10, the currently used high energy density fuel, by mixing in the proportions described in Table 2, which Table also includes the product properties for the blends. When 30 to 60 weight percent of the dimer (II) was blended with JP-10, the resulting liquid blends had higher energy density by 2–7% than the JP-10 base fuel (Table 2).

For the blends of the invention it has been discovered that both the net volumetric heat of combustion and density are linear functions of the amount of norbornene cyclodimer in the blend. At 100 wt % JP-10 fuel, the net heat of combustion is about 141,436 btu/gal while at 100 wt % dimer the net heat of combustion is about 151,810 btu/gal. A blend of the two components containing about 60 wt % dimer has a net heat of combustion of about 147,888 btu/gal. JP-10 fuel density is about 0.935. Based on the linear relationship between density and the dimer content in the blends with JP-10, the "equivalent" liquid density of the pure dimer was calculated to be 1.105 g/cc.

TABLE 2

Properties of the Blends of Norbornene dimer in JP-10

| w % dimer | 100% (dimer) | 60% | 50% | 40% | 30% | 0%(JP-10) |
|---|---|---|---|---|---|---|
| Density | 1.015 | 0.984 | 0.974 | 0.967 | 0.959 | 0.935 |
| Net Btu/lb | 17,923 | 18,010 | 18,043 | 17,998 | 18,036 | 18,127 |
| Vol. Heat Btu/gal | 151,810 | 147,888 | 146,653 | 145,236 | 144,338 | 141,438 |
| Gain over JP-10 | 7% | 5% | 4% | 3% | 2% | — |
| Pour Pt., (°C.) | — | 0 | −10 | <−40 | <−40 | <−40 |

The process of the invention is more effective in the dimerization of norbornadiene (III) over $Cr/SiO_2$ in a manner analogous to the dimerization of norbornene (I) with catalyst turn over number at least of 2000. The dimerization of norbornadiene (III) with $Cr/SiO_2$ produces pentacyclo [8.2.1.1$^{4,7}$.0$^{2,9}$.0$^{3,8}$]-tetradecadiene-5,11 (IV), primarily in the conformation of the exo-trans-exo isomer with minor amounts of the exo-trans-endo and endo-transendo isomers. The preparation of norbornadiene dimer according to the process of the invention is described in Example G.

EXAMPLE G

A solution of norbornadiene in hexane (25 gms in 10 gms) was added to a suspension of $Cr/SiO_2$ in hexane (1 gm in 5 gms) at room temperature. The exothermic reaction started and the temperature rose to 60° C. quickly. The reaction temperature was controlled at 60° C. for three hours. Work up yielded 24 gms of white solid dimers of norbornadiene comprising pentacyclo $[8.2.1.1^{4,7}.0^{2,9}.0^{3,8}]$-tetradecadiene-5,11 (IV). The structure of the dimer (IV) and isomers were confirmed by $^{13}C$ NMR and comparison of 1H-NMR with literature values.

EXAMPLE H

Norbornadiene dimer was hydrogenated using 5 weight percent Pd/C at 15 psi and room temperature to give a saturated compound which has an identical $^{13}C$ NMR to that of norbornene dimer (II).

The dimerization of norbornene according to the process of the invention can be carried out between 0° and 200° C., but preferably about 60° to 100° C. The dimerization of norbornadiene according to the process of the invention can be carried out between 0° and 200 ° C., but preferably about 40° to 80° C.

What is claimed is:

1. A process for the dimerization of norbornene to produce pentacyclo $[8.2.1.1^{4,7}.0^{2,9}.0^{3,8}]$-tetradecane with high stereoselectivity comprising:

contacting said norbornene with a reduced chromium oxide catalyst on a porous $SiO_2$ support under dimerization conditions whereby said $[8.2.1.1^{4,7}.0^{2,9}.0^{3,8}]$-tetradecane is produced comprising at least 90 weight percent of the exo-trans-exo isomer.

2. The process of claim 1 wherein said catalyst comprises CO, $H_2$ or metal alkyl reduced $CrO_3$ and said support comprises silica having a pore size of at least 20 Angstroms.

3. The process of claim 1 wherein said dimerization conditions comprise temperature between 0° C. and 200° C.

4. The process of claim 3 wherein said temperature is between 80° C. and 100° C.

5. A process for the dimerization of norbornadiene to produce pentacyclo $[8.2.1.1^{4,7}.0^{2,9}.0^{3,8}]$-tetradecadiene-5,11 with high stereo selectivity comprising:

contacting said norbornadiene with a reduced chromium oxide catalyst on a porous $SiO_2$ support under dimerization conditions whereby said $[8.2.1.1^{4,7}.0^{2,9}.0^{3,8}]$-tetradecadiene-5,11 is produced comprising primarily the exo-trans-exo isomer.

6. The process of claim 5 wherein said catalyst comprises CO, $H_2$ or metal alkyl reduced $CrO_3$ and said support comprises silica having a pore size of at least 40 Angstroms.

7. The process of claim 5 wherein said dimerization conditions comprise temperature between 0° C. and 200° C.

8. The process of claim 9 wherein said temperature is between 80° C. and 100° C.

9. The process of claim 7 wherein at least 90 weight percent of said $[8.2.1.1^{4,7}.0^{2,9}.0^{3,8}]$-tetradecane consists of the exo-trans-exo isomer.

* * * * *